(12) United States Patent
Parthasaradhi Reddy et al.

(10) Patent No.: US 10,206,874 B2
(45) Date of Patent: Feb. 19, 2019

(54) RUFINAMIDE SOLID DISPERSION

(71) Applicant: HETERO RESEARCH FOUNDATION, Hyderabad, Andhra Pradesh (IN)

(72) Inventors: Bandi Parthasaradhi Reddy, Hyderabad (IN); Kura Rathnakar Reddy, Hyderabad (IN); Dasari Muralidhara Reddy, Hyderabad (IN); Kesireddy Subash Chander Reddy, Hyderabad (IN); Bandi Vamsi Krishna, Hyderabad (IN)

(73) Assignee: Hetero Research Foundation (IN)

( * ) Notice: Subject to any disclaimer, the term of this patent is extended or adjusted under 35 U.S.C. 154(b) by 15 days.

(21) Appl. No.: 14/590,432

(22) PCT Filed: Jul. 18, 2013

(86) PCT No.: PCT/IN2013/000446
§ 371 (c)(1),
(2) Date: Jan. 6, 2015

(87) PCT Pub. No.: WO2014/013511
PCT Pub. Date: Jan. 23, 2014

(65) Prior Publication Data
US 2015/0182458 A1    Jul. 2, 2015

(30) Foreign Application Priority Data

Jul. 20, 2012   (IN) .......................... 2972/CHE/2012

(51) Int. Cl.
*A61K 9/10* (2006.01)
*A61K 31/4192* (2006.01)
*A61K 47/38* (2006.01)
*A61K 9/16* (2006.01)
*A61K 47/10* (2017.01)
*A61K 47/32* (2006.01)

(52) U.S. Cl.
CPC .............. *A61K 9/10* (2013.01); *A61K 9/1694* (2013.01); *A61K 31/4192* (2013.01); *A61K 47/10* (2013.01); *A61K 47/32* (2013.01); *A61K 47/38* (2013.01); *A61K 9/1635* (2013.01); *A61K 9/1641* (2013.01); *A61K 9/1652* (2013.01)

(58) Field of Classification Search
None
See application file for complete search history.

(56) References Cited

U.S. PATENT DOCUMENTS

| 5,955,475 A | 9/1999 | Krape et al. |
| 8,076,362 B2 | 12/2011 | Portmann et al. |
| 2010/0239667 A1 | 8/2010 | Hemmingsen et al. |
| 2011/0034523 A1 | 2/2011 | Razzetti et al. |

FOREIGN PATENT DOCUMENTS

| EP | 2105130 A1 | 9/2009 |
| WO | 2014013511 A2 | 1/2014 |
| WO | 2014013511 A3 | 1/2014 |

OTHER PUBLICATIONS

Douroumis et al., Journal of Pharmacy and Pharmacology, 2007, 59: 645-653.*
International Written Opinion of PCT/IN2013/000446 dated Jan. 17, 2014.
International Search Report of PCT/IN2013/000446 dated Jan. 17, 0214.
Soluplus, Technical Information, BASF The Chemical Company, Jul. 2010.
Span and Tween, Croda Europe Ltd., Aug. 2010.

* cited by examiner

*Primary Examiner* — Alicia L Otton
(74) *Attorney, Agent, or Firm* — Caesar Rivise, PC

(57) ABSTRACT

The present invention provides a solid dispersion of rufinamide in combination with a pharmaceutically acceptable carrier, process for its preparation and pharmaceutical compositions comprising it.

7 Claims, 1 Drawing Sheet

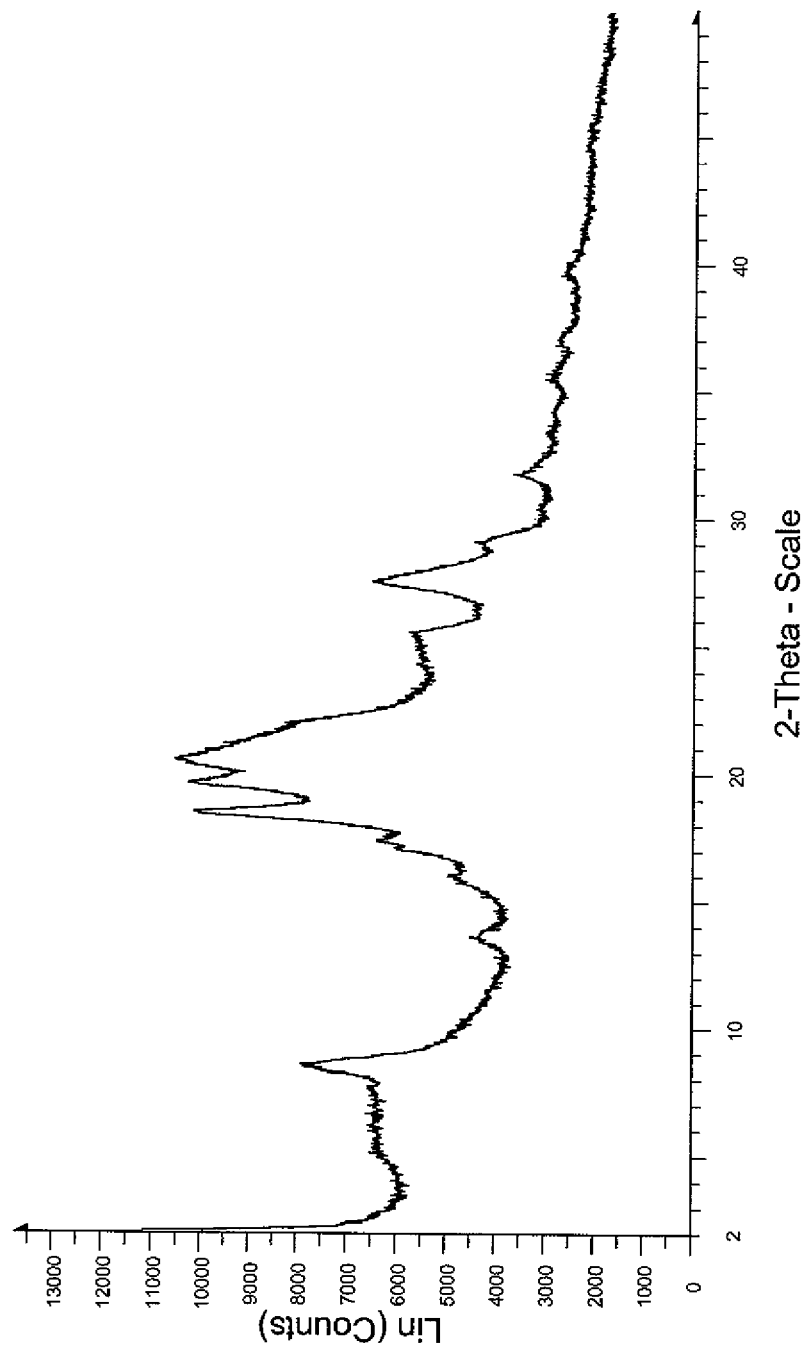

RUFINAMIDE SOLID DISPERSION

This application claims the benefit of Indian Provisional Patent Application No. 2972/CHE/2012, filed on Jul. 20, 2012, which is incorporated herein by reference.

FIELD OF THE INVENTION

The present invention provides a solid dispersion of rufinamide in combination with a pharmaceutically acceptable carrier, process for its preparation and pharmaceutical compositions comprising it.

BACKGROUND OF THE INVENTION

Rufinamide is chemically, 1-[(2,6-Difluorophenyl)methyl]-1H-1,2,3-triazole-4-carboxamide and has the structural formula:

Rufinamide is an anticonvulsant medication. It is used in combination with other medication and therapy to treat Lennox-Gastaut syndrome and various other seizure disorders. It is marketed under the brand name Banzel® by EISAI INC.

Rufinamide and its process were disclosed in European patent no. 199262.

Polymorphism is defined as "the ability of a substance to exist as two or more crystalline phases that have different arrangement and/or conformations of the molecules in the crystal Lattice. Thus, in the strict sense, polymorphs are different crystalline structures of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning calorimetry (DSC) and Infrared spectrometry (IR).

Solvent medium and mode of crystallization play very important role in obtaining one polymorphic Form over the other.

Rufinamide can exist in different polymorphic Forms, which may differ from each other in terms of stability, physical properties, spectral data and methods of preparation.

U.S. Pat. No. 6,740,669 disclosed crystal modification A and A' of rufinamide.

European patent no. 0994864 disclosed crystal modification B and C of rufinamide.

Form α and β of rufinamide were disclosed in European patent application no. 2292609 ('609 patent). According to the '609 patent, Form α can be characterized by the 2θ values at 4.5, 9.0, 13.5, 18.0, 18.8, 19.5, 20.6, 24.6, 25.7, 26.5, 27.4, 27.9, 28.7, 30.0 and 31.8±0.2 degrees.

According to the '609 patent, Form β can be characterized by the 2θ values at 6.4, 12.7, 17.7, 18.5, 19.1, 22.2, 22.8, 24.2, 26.5, 28.9, 29.4, 32.1 and 34.3±0.2 degrees.

International patent application publication no. WO 2011/135105 disclosed crystalline Form R-5 of rufinamide.

We have found a solid dispersion of rufinamide in combination with a pharmaceutically acceptable carrier. The solid dispersion of rufinamide is stable, reproducible and amicable for large scale preparation.

Thus, an object of the present invention is to provide a solid dispersion of rufinamide in combination with a pharmaceutically acceptable carrier, process for its preparation and pharmaceutical compositions comprising it.

SUMMARY OF THE INVENTION

In one aspect, the present invention provides a solid dispersion of rufinamide in combination with a pharmaceutically acceptable carrier. Preferably, the ratio of rufinamide to the pharmaceutically acceptable carrier is 1:0.8 to 1:2.0.

Preferably, the pharmaceutically acceptable carriers may be one or more of copovidone, SPAN®20 (sorbitan laurate), ethyl cellulose, hydroxypropyl methylcellulose, polyethylene glycol or SOLUPLUS® (polyvinyl caprolactam-polyvinyl acetate-polyethylene glycol graft copolymer).

In another aspect, the present invention there is provided a process for the preparation of solid dispersion of rufinamide in combination with a pharmaceutically acceptable carrier, which comprises:
  a) preparing a solution comprising a mixture of rufinamide and one or more pharmaceutically acceptable carriers selected from copovidone, SPAN®20 (sorbitan laurate), ethyl cellulose, hydroxypropyl methylcellulose, polyethylene glycol or SOLUPLUS® (polyvinyl caprolactam-polyvinyl acetate-polyethylene glycol graft copolymer) in a solvent; and
  b) removing the solvent from the solution to obtain a solid dispersion of rufinamide in combination with a pharmaceutically acceptable carrier.

Yet in another aspect, the present invention provides pharmaceutical compositions comprising a therapeutically effective amount of solid dispersion of rufinamide along with a pharmaceutically acceptable carrier, and at least one pharmaceutically acceptable excipient.

BRIEF DESCRIPTION OF THE DRAWING

FIG. 1 is a powder X-ray diffractogram patterns of solid dispersion of rufinamide in combination with a pharmaceutically acceptable carrier.

Powder X-ray diffraction spectrum was measured on a bruker AXS D8 advance powder X-ray diffractometer having a copper-Kα radiation. Approximately 1 gm of sample was ground powder on a sample holder and scanned from 2 to 50 degrees two-theta, at 0.020 degrees two theta per step and a step time of 1 second. The sample was simply placed on the sample holder. The sample was rotated at 30 rpm at a voltage 40 kV and current 35 mA.

DETAILED DESCRIPTION OF THE INVENTION

The term "room temperature" refers to temperature at about 25 to 35° C.

According to one aspect of the present invention, there is provided a solid dispersion of rufinamide in combination with a pharmaceutically acceptable carrier. Preferably, the ratio of rufinamide to the pharmaceutically acceptable carrier is 1:0.8 to 1:2.0 and more preferably the ratio is 1:1 to 1:1.8.

The powdered x-ray diffractogram (PXRD) of solid dispersion of rufinamide in combination with a pharmaceutically acceptable carrier is shown in FIG. 1.

Solid dispersion of rufinamide in combination with a pharmaceutically acceptable carrier is found to be stable.

Preferably, the pharmaceutically acceptable carriers may be one or more of copovidone, SPAN®20 (sorbitan laurate), ethyl cellulose, hydroxypropyl methylcellulose, polyethylene glycol or SOLUPLUS® (polyvinyl caprolactam-polyvinyl acetate-polyethylene glycol graft copolymer). More preferably the pharmaceutically acceptable carriers are copovidone, span 20 and hydroxypropyl methylcellulose.

According to another aspect of the present invention, there is provided a process for the preparation of solid dispersion of rufinamide in combination with a pharmaceutically acceptable carrier, which comprises:

a) preparing a solution comprising a mixture of rufinamide and one or more pharmaceutically acceptable carriers selected from copovidone, SPAN®20 (sorbitan laurate), ethyl cellulose, hydroxypropyl methylcellulose, polyethylene glycol or SOLUPLUS® (polyvinyl caprolactam-polyvinyl acetate-polyethylene glycol graft copolymer) in a solvent; and b) removing the solvent from the solution to obtain a solid dispersion of rufinamide in combination with a pharmaceutically acceptable carrier.

Rufinamide used in step (a) may preferably be rufinamide obtained by the known process.

The solvent used in step (a) may preferably be a solvent or a mixture of solvents selected from dimethyl sulfoxide, dimethylacetamide, dimethylformamide, methanol, ethanol, isopropanol, n-butanol and n-pentanol, and more preferably the solvents are dimethyl sulfoxide, dimethylacetamide, dimethylformamide and n-butanol.

Preferably, the pharmaceutically acceptable carriers used in step (a) may be selected form copovidone, SPAN®20 (sorbitan laurate) and hydroxypropyl methylcellulose.

The solvent may be removed from the solution in step (b) by known methods, for example, distillation, freeze drying or spray drying.

The distillation of the solvent may be carried out at atmospheric pressure or at reduced pressure. The distillation may preferably be carried out until the solvent is almost completely distilled off.

As used herein, "reduced pressure" refers to a pressure of less than 100 mmHg.

According to another aspect of the present invention, there is provided pharmaceutical compositions comprising a therapeutically effective amount of solid dispersion of rufinamide along with a pharmaceutically acceptable carrier, and at least one pharmaceutically acceptable excipient. The solid dispersion of rufinamide may preferably be formulated into tablets, capsules, suspensions, dispersions, injectables or other pharmaceutical forms.

The invention will now be further described by the following examples, which are illustrative rather than limiting.

EXAMPLES

Example 1

Preparation of Rufinamide

Ethyl 1-(2,6-difluorobenzyl)-1H-1,2,3-triazole-4-carboxylate (10 Kg) was dissolved in methanol (75 L) and then heated to 50 to 55° C. To the reaction mixture was passed ammonia gas continuously and then maintained for 24 hours. The reaction mass was then cooled to room temperature and maintained for 2 hours. The separated solid was filtered and then dried to obtain a solid. To the solid was added formic acid (39 L) and then heated to 50 to 55° C. The solution was then cooled to 20 to 25° C. and then added methanol (40 L). The reaction mass was maintained for 2 hours at 20 to 25° C. and filtered. The solid obtained was dried to obtain 7.2 Kg of rufinamide.

Example 2

Preparation of Rufinamide Solid Dispersion with Hydroxypropyl Methylcellulose

A mixture of rufinamide (10 Kg) as obtained in example 1 and hydroxypropyl methylcellulose (15 Kg) was dissolved in n-butanol (500 L) at room temperature. The contents were then heated to reflux and stirred for 1 hour to obtain a clear solution. The solvent was distilled off under vacuum at below 80° C. and then dried to obtain 24.5 Kg of rufinamide solid dispersion with hydroxypropyl methylcellulose.

Example 3

Preparation of Rufinamide Solid Dispersion with Hydroxypropyl Methylcellulose

A mixture of rufinamide (10 Kg) and hydroxypropyl methylcellulose (10 Kg) was dissolved in n-butanol (400 L) at room temperature. The contents were then heated to reflux and stirred for 1 hour to obtain a clear solution. The solvent was distilled off under vacuum at below 80° C. and then dried to obtain 19.5 Kg of rufinamide solid dispersion with hydroxypropyl methylcellulose.

Example 4

Preparation of Rufinamide Solid Dispersion with Hydroxypropyl Methylcellulose

A mixture of rufinamide (10 Kg) and hydroxypropyl methylcellulose (18 Kg) was dissolved in n-butanol (600 L) at room temperature. The contents were then heated to reflux and stirred for 1 hour to obtain a clear solution. The solvent was distilled off under vacuum at below 80° C. and then dried to obtain 27 Kg of rufinamide solid dispersion with hydroxypropyl methylcellulose.

Example 5

Preparation of Rufinamide Solid Dispersion with Hydroxypropyl Methylcellulose

Example 2 was repeated using dimethylacetamide solvent instead of n-butanol solvent to obtain rufinamide solid dispersion with hydroxypropyl methylcellulose.

Example 6

Preparation of Rufinamide Solid Dispersion with Hydroxypropyl Methylcellulose

Example 2 was repeated using dimethyl sulfoxide solvent instead of n-butanol solvent to obtain rufinamide solid dispersion with hydroxypropyl methylcellulose.

Example 7

Preparation of Rufinamide Solid Dispersion with Hydroxypropyl Methylcellulose

Example 2 was repeated using isopropanol solvent instead of n-butanol solvent to obtain rufinamide solid dispersion with hydroxypropyl methylcellulose.

Example 8

Preparation of Rufinamide Solid Dispersion with Copovidone

A mixture of rufinamide (10 Kg) and copovidone (15 Kg) was dissolved in n-butanol (500 L) at room temperature. The contents were then heated to reflux and stirred for 1 hour to obtain a clear solution. The solvent was distilled off under vacuum at below 80° C. and then dried to obtain 24 Kg of rufinamide solid dispersion with copovidone.

Example 9

Preparation of Rufinamide Solid Dispersion with Copovidone

Example 8 was repeated using dimethylacetamide solvent instead of n-butanol solvent to obtain rufinamide solid dispersion with copovidone.

Example 10

Preparation of Rufinamide Solid Dispersion with Copovidone

Example 8 was repeated using dimethylformamide solvent instead of n-butanol solvent to obtain rufinamide solid dispersion with copovidone.

Example 11

Preparation of Rufinamide Solid Dispersion with Copovidone

Example 8 was repeated using dimethyl sulfoxide solvent instead of n-butanol solvent to obtain rufinamide solid dispersion with copovidone.

Example 12

Preparation of Rufinamide Solid Dispersion with Polyethylene Glycol

A mixture of rufinamide (10 Kg) and polyethylene glycol (15 Kg) was dissolved in n-butanol (500 L) at room temperature. The contents were then heated to reflux and stirred for 1 hour to obtain a clear solution. The solvent was distilled off under vacuum at below 80° C. and then dried to obtain 23.5 Kg of rufinamide solid dispersion with polyethylene glycol.

Example 13

Preparation of Rufinamide Solid Dispersion with SOLUPLUS® (Polyvinyl Caprolactam-Polyvinyl Acetate-Polyethylene Glycol Graft Copolymer)

A mixture of rufinamide (10 Kg) and soluplus (15 Kg) was dissolved in n-butanol (500 L) at room temperature. The contents were then heated to reflux and stirred for 1 hour to obtain a clear solution. The solvent was distilled off under vacuum at below 80° C. and then dried to obtain 23.5 Kg of rufinamide solid dispersion with SOLUPLUS® (polyvinyl caprolactam-polyvinyl acetate-polyethylene glycol graft copolymer).

Example 14

Preparation of Rufinamide Solid Dispersion with Hydroxypropyl Methylcellulose

Ethyl 1-(2,6-difluorobenzyl)-1H-1,2,3-triazole-4-carboxylate (10 Kg) was dissolved in methanol (75 L) and then heated to 50 to 55° C. To the reaction mixture was passed ammonia gas continuously and then maintained for 24 hours. The reaction mass was then cooled to room temperature and maintained for 2 hours. The separated solid was filtered and then dried to obtain a solid. To the solid was added formic acid (39 L) and then heated to 50 to 55° C. The solution was then cooled to 20 to 25° C. and then added methanol (40 L). The reaction mass was maintained for 2 hours at 20 to 25° C. and then added a mixture of hydroxypropyl methylcellulose (12 Kg) and n-butanol (400 L). The contents were then heated to reflux and stirred for 1 hour to obtain a clear solution. The solvent was distilled off under vacuum at below 80° C. and then dried to obtain 18.9 Kg of rufinamide solid dispersion with hydroxypropyl methylcellulose.

Example 15

Preparation of Rufinamide Solid Dispersion with Hydroxypropyl Methylcellulose

Ethyl 1-(2,6-difluorobenzyl)-1H-1,2,3-triazole-4-carboxylate (10 Kg) was dissolved in methanol (75 L) and then heated to 50 to 55° C. To the reaction mixture was passed ammonia gas continuously and then maintained for 24 hours. The reaction mass was then cooled to room temperature and maintained for 2 hours. The separated solid was filtered and then dried to obtain a solid. To the solid was added formic acid (39 L) and then heated to 50 to 55° C. The solution was then cooled to 20 to 25° C. and then added methanol (40 L). The reaction mass was maintained for 2 hours at 20 to 25° C. and then added a mixture of hydroxypropyl methylcellulose (12 Kg) and n-butanol (300 L). The contents were then heated to reflux and stirred for 1 hour to obtain a clear solution. The solvent was distilled off under vacuum at below 80° C. and then dried to obtain 18.5 Kg of rufinamide solid dispersion with hydroxypropyl methylcellulose.

Example 16

Preparation of Rufinamide Solid Dispersion with Copovidone

Ethyl 1-(2,6-difluorobenzyl)-1H-1,2,3-triazole-4-carboxylate (10 Kg) was dissolved in methanol (75 L) and then heated to 50 to 55° C. To the reaction mixture was passed ammonia gas continuously and then maintained for 24 hours. The reaction mass was then cooled to room temperature and maintained for 2 hours. The separated solid was filtered and then dried to obtain a solid. To the solid was added formic acid (39 L) and then heated to 50 to 55° C. The solution was then cooled to 20 to 25° C. and then added methanol (40 L). The reaction mass was maintained for 2 hours at 20 to 25° C. and then added a mixture of copovidone (12 Kg) and n-butanol (400 L). The contents were then heated to reflux and stirred for 1 hour to obtain a clear solution. The solvent was distilled off under vacuum at below 80° C. and then dried to obtain 18.4 Kg of rufinamide solid dispersion with copovidone.

We claim:

1. A solid dispersion of rufinamide in combination with a pharmaceutically acceptable carrier, wherein the pharmaceutically acceptable carrier is hydroxypropyl methylcellulose, further wherein the solid dispersion of rufinamide in combination with the pharmaceutically acceptable carrier has a powder X-ray diffractogram when measured using copper-Kalpha radiation as shown in FIG. 1.

2. The solid dispersion of claim 1, wherein the ratio of rufinamide to the pharmaceutically acceptable carrier is 1:1 to 1:1.8.

3. A pharmaceutical composition comprising a therapeutically effective amount of a solid dispersion of rufinamide in combination with a pharmaceutically acceptable carrier, wherein the pharmaceutically acceptable carrier is hydroxypropyl methylcellulose, further wherein the solid dispersion of rufinamide in combination with the pharmaceutically acceptable carrier has a powder X-ray diffractogram when measured using copper-Ka radiation as shown in FIG. 1, and at least one pharmaceutically acceptable excipient.

4. The pharmaceutical composition as claimed in claim 3, wherein the solid dispersion of rufinamide is formulated into tablets, capsules, suspensions, dispersions or injectables.

5. A process for the preparation of the solid dispersion of rufinamide in combination with a pharmaceutically acceptable carrier of claim 1, which comprises:
   a. preparing a solution comprising a mixture of rufinamide and the pharmaceutically acceptable carrier hydroxypropyl methylcellulose in a solvent; and
   b. removing the solvent from the solution to obtain a solid dispersion of rufinamide in combination with a pharmaceutically acceptable carrier, wherein the rufinamide has a powder X-ray diffractogram when measured using copper-Kalpha radiation as shown in FIG. 1.

6. The process as claimed in claim 5, wherein the solvent used in step (a) is a solvent or a mixture of solvents selected from dimethyl sulfoxide, dimethylacetamide, dimethylformamide, methanol, ethanol, isopropanol, n-butanol and n-pentanol.

7. The process as claimed in claim 6, wherein the solvents are dimethyl sulfoxide, dimethylacetamide, dimethylformamide and n-butanol.

* * * * *